United States Patent [19]

Cohen

[11] 4,421,508
[45] * Dec. 20, 1983

[54] VACUUM-COMPRESSION INJECTOR

[76] Inventor: Edgar C. Cohen, 4123 Vincennes Pl., New Orleans, La. 70125

[ * ] Notice: The portion of the term of this patent subsequent to Sep. 13, 2000 has been disclaimed.

[21] Appl. No.: 281,436

[22] Filed: Jul. 8, 1981

Related U.S. Application Data

[63] Continuation-in-part of Ser. No. 237,563, Feb. 24, 1981.

[51] Int. Cl.³ .............................................. A61M 5/30
[52] U.S. Cl. ........................................ 604/70; 604/72
[58] Field of Search ...................... 128/207.25, 207.24, 128/207.23, 218 A, 218 R, 218 F, 215, DIG. 1, 272; 604/70, 72

[56] References Cited

U.S. PATENT DOCUMENTS

| 1,934,046 | 11/1933 | Demarchi | 128/215 |
|---|---|---|---|
| 2,743,723 | 5/1956 | Hein | 128/215 |
| 2,945,496 | 7/1960 | Fosdal | 128/215 |
| 3,057,349 | 10/1962 | Ismach | 128/207.23 |
| 3,140,713 | 7/1964 | Ismach | 128/207.23 |
| 3,167,071 | 1/1965 | Venditty | 128/207.25 |
| 3,189,029 | 6/1965 | Stephens | 128/207.25 |
| 3,424,154 | 1/1969 | Kinsley | 128/207.25 |
| 3,490,451 | 1/1970 | Yahner | 128/207.23 |
| 3,515,130 | 6/1970 | Tsujino | 128/207.25 |
| 3,548,830 | 12/1970 | Goey | 128/361 |
| 3,688,765 | 9/1972 | Gasaway | 128/207.25 |
| 3,933,155 | 1/1976 | Johnston | 128/207.23 |
| 3,945,383 | 3/1976 | Bennett et al. | 128/207.25 |
| 4,284,077 | 8/1981 | Wagner | 128/215 |

FOREIGN PATENT DOCUMENTS 957598 2/1957 Fed. Rep. of Germany ........................ 128/207.25

*Primary Examiner*—Henry J. Recla
*Attorney, Agent, or Firm*—Griffin, Branigan & Butler

[57] ABSTRACT

A needleless vacuum-compression injector applies a continuous vacuum between a medicament holder and an outwardly extending member spaced therefrom. The continuous vacuum holds tissue taut and immobilizes the tissue over a nozzle without puncturing the tissue. Pressurized gas then injects the medicament into the tissue to a predetermined depth determined by the pressure of the gas. The outwardly extending member can be a removable sleeve. Particularly for oral applications, the tissue-engaging surface of the outwardly extending member can be oval or otherwise non-circular in shape to accommodate the shape of the tissue to be injected.

12 Claims, 8 Drawing Figures

U.S. Patent    Dec. 20, 1983    Sheet 1 of 2    4,421,508
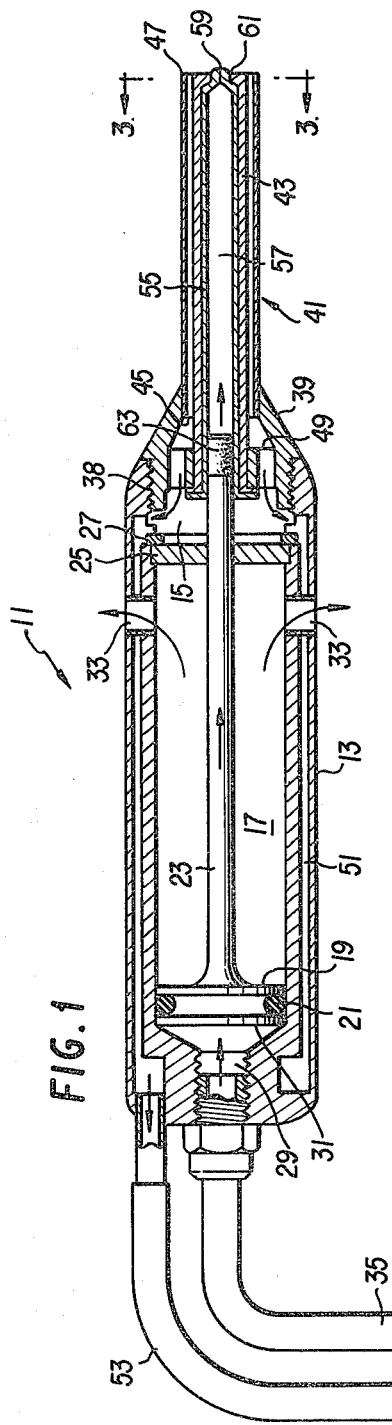
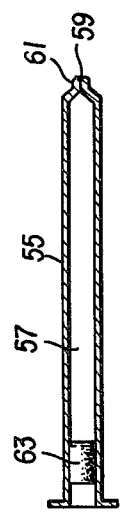
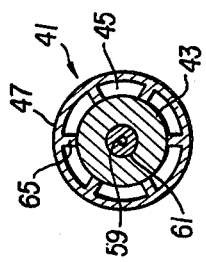
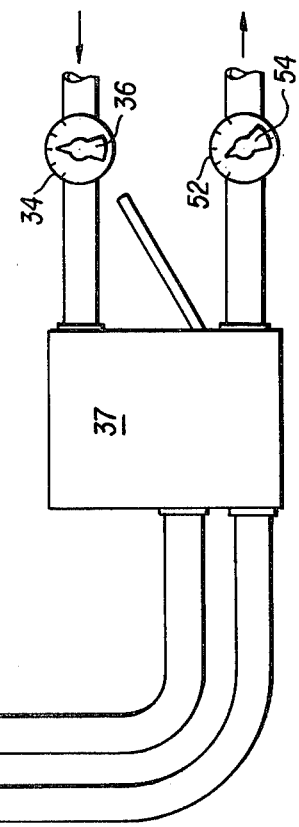

VACUUM-COMPRESSION INJECTOR

This application is a continuation-in-part of U.S. Ser. No. 237,563, filed Feb. 24, 1981.

This invention is in the field of hypodermic and hypomucosal injectors using pressurized air to force a medicament into the tissue.

BACKGROUND

The concept of using pressurized air to inject a fluid through the skin of a human being or an animal is not new. U.S. Pat. No. 3,140,713 to Ismach, for example, discloses a conventional jet injection device with an intradermal nozzle designed to inject fluid at an angle of 45° to control the depth of penetration and prevent tearing or rupturing of the skin. In this regard, it has been found that the pressure entry of liquid into non-fixed, movable soft tissue at various angles creates undesirable tearing, hemorrhage and subsequent post-operative pain. As a result, the use of existing jet injectors have not overcome the physical and psychological traumatic effects of a syringe and needle—particularly in the field of oral injections into mucosa.

SUMMARY

The present invention overcomes the above objections to jet hypodermic injector devices by using a vacuum to stabilize a nozzle of the device over the tissue to be penetrated. In this respect, the suction pulls the tissue taut and draws it over an orifice of the nozzle so that the nozzle and tissue are essentially immobile relative to each other. This then eliminates the entry of medicament liquids at various angles; eliminates the resultant tearing of the soft tissue; and, reduces the accompanying pain. The structure of the invention also includes an air driven piston which provides for a smooth delivery of the medicament into the tissue and precludes the undesirable shock wave that is generated in the soft tissue by prior art spring-driven-piston devices.

In addition, structure of the invention includes a means for regulating the air pressure exerted on the air driven piston in order to control the depth of penetration of the medicament into the tissue. The vacuum pressure is also controllable.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout different views. The drawings are not necessarily to scale, emphasis instead being placed upon illustrating principles of the invention.

FIG. 1 is a partial cross-sectional view of a vacuum compression injector according to principles of this invention;

FIG. 2 is a schematic partial cross-sectional view of a medicament insert; and,

FIG. 3 is a cross-sectional view of an embodiment of the invention taken along lines 3—3 of FIG. 1;

DESCRIPTION OF PREFERRED EMBODIMENTS

Figure 4:
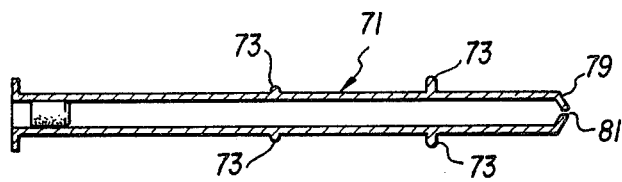
FIG. 4 is a schematic partial cross-sectional view of an alternate embodiment of a medicament insert.

A vacuum-compression injector 11 of the invention is illustrated in FIG. 1. Therein, an exterior cylindrical housing 13 contains a vacuum chamber 15 and an interior cylindrical chamber 17. The interior cylindrical chamber 17 contains a movable piston 19 with an o-ring 21 providing an air-tight seal between the piston 19 and the interior of cylindrical chamber 17. The piston 19 has a piston rod or plunger 23 extending forwardly in the interior chamber 17 and maintained in an axial position by a guide bushing 25 which is held in position by a retaining ring 27 at the right end of the interior chamber 17 in FIG. 1.

The other end of the interior cylindrical chamber 17 contains a port 29 through which air under pressure enters and impinges upon a face 31 of the piston 19.

The right end of the interior cylindrical chamber 17 adjacent to the piston rod guide bushing 25 has a plurality of vents 33 opening through the cylindrical housing 13 to the atmosphere.

The air supply port 29 is connected by an air supply line 35 to a two-phase pneumatic switch 37 which, in turn, is connected through an air pressure regulator valve 34 to an air supply source (not shown). The air pressure regulator valve 34 has a dial with a central handle 36 to regulate the air pressure to the switch 37 and the supply line 35.

The right end of the cylindrical housing 13 in FIG. 1 has interior threads 38 for threadably joining the tapered base 39 of a generally cylindrical nozzle housing 41. The cylindrical nozzle housing 41 contains a hollow concentric cylindrical medicament-insert-holder 43 which is spaced from the interior of the cylindrical housing 41 leaving an annular passageway 45 extending from a forward end 47 of the housing 41 back through a plurality of vacuum ports 49 to the vacuum chamber 15. The vacuum chamber 15 is connected to a second annular passageway 51 contained within the cylindrical housing 13. This second passageway 51 extends to the end of the housing 13 where it joins a vacuum line 53. The vacuum line 53 is connected through the two phase pneumatic switch 37 and a vacuum pressure regulator valve 52 to a source of vacuum (not shown). The vacuum pressure regulator valve 52 has a dial with a control handle 54 to regulate the vacuum pressure to the switch 37 and the vacuum line 53.

A cylindrical medicament insert 55 (FIG. 2) has an interior cavity 57 for storing a supply of medicament. The medicament insert 55 has an orifice 59 at its forward end 61 and is sealed at its other end by a plunger-plug 63.

As can be seen in FIG. 3, the forward end 47 of the nozzle housing 41 is spaced from the medicament insert holder 43 by a plurality of spacers 65 defining the annular vacuum passageway 45. The forward end 61 of the medicament insert 55 protrudes through the forward end wall of the insert holder 43, as shown in FIGS. 1 and 3.

The medicament orifice 59 in the insert 55 is centrally located in the forward end 61 of the insert 55 to form a nozzle as can be seen in FIGS. 2 and 3. In an alternative embodiment, not shown, the nozzle is formed integrally with the holder 43 and the insert 55 located therebehind but; of course, in communication with the passageway leading to orifice 59. In still another alternative embodiment, the insert is essentially stationary with medicament being supplied thereto from an outside source as required.

Figure 5:
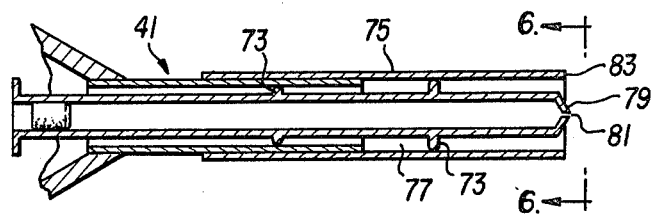
FIG. 5 is a schematic partial cross-sectional view of a FIG. 4 embodiment installed in the housing of FIG. 1 and surrounded by a removable sleeve.
Figure 6:
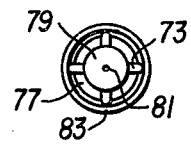
FIG. 6 is a view of FIG. 5 taken along the lines 6—6 thereof.

In another embodiment as illustrated in FIGS. 4, 5, and 6, a disposable medicament insert 71 has a plurality of nodules 73 positioned about the periphery of its outer surface. The nodules 73 hold the medicament insert 71 in position inside the nozzle housing 41 and a removable forward-end section 75 which is slidably or threadably engaged in the housing 41. The nodules 73 provide spacing between the medicament insert 71 and the nozzle housing 41 and its forward end section 75 for an annular vacuum passageway 77. A forward end 79 of the medicament insert 71 contains an orifice 81 and protrudes beyond a cylindrical end 83 of the removable forward end section 75 of the nozzle housing 41.

Figure 7:
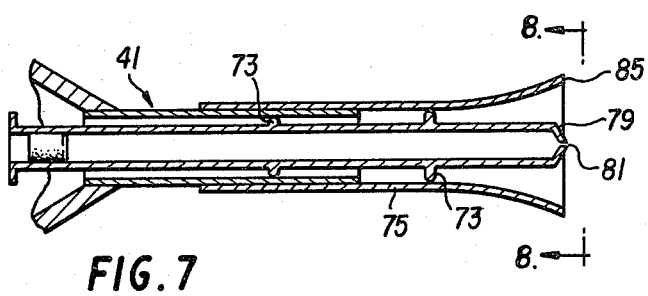
FIG. 7 is an alternate embodiment of the FIG. 5 structure.
Figure 8:
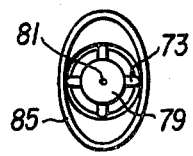
FIG. 8 is a view of the FIG. 7 structure taken along the lines 8—8 thereof.

In still another embodiment as illustrated in FIGS. 7 and 8, the removable forward-end section 75 of the nozzle housing 41 has an oval-shaped end 85 or the like to permit access to somewhat elongated surface areas in an oral cavity, for example. Other end-shapes are used to accommodate confined or other areas into which medicament is to be injected.

The medicament inserts shown in FIGS. 4 through 8 may be constructed from a plastic, or a metal or the like and are preferably disposable.

In operation, with a medicament insert 55 in position within the holder 43 of the nozzle housing 41, the two phase pneumatic switch 37 is initially depressed halfway to open the vacuum source through line 53 and intervening passageway 51, chamber 15, and passageway 45 to the forward end 47 of the nozzle housing 41 to draw a patient's tissue firmly over the forward end 61 of the medicament insert 55 and its orifice 59. In this manner the tissue is immobilized. The two phase pneumatic switch 37 is then fully depressed to release a charge of compressed air through line 35 to impinge upon the piston face 31 driving the piston 19 forward in the interior chamber 17. At the same time the piston rod 23 drives the plunger-plug 63 forward in the medicament insert 55 forcing the medicament out through the passageway leading to orifice 59 (and orifice 59 itself) with sufficient force to penetrate the soft tissue of the patient. As this occurs air trapped forward of the piston 19 is exhausted from the chamber 17 through the vents 33 to the atmosphere.

The depth of penetration of the medicament into the tissue of the patient is controlled by adjusting the control handle 36 of the air pressure regulator valve 34. This adjustment is made by reference to the dial on the regulator 34 prior to actuation of the switch 37. In this respect, it has been found that in one embodiment the depth of penetration was limited to only ¼ centimeter at a pressure of 20 psi but extended to 8.9 centimeters at a pressure of 110 psi, with different depths of penetration, of course, resulting from different pressures in between.

After the injection has been completed, the nozzle housing 41 is unscrewed from the cylindrical housing 13 and the cylindrical medicament insert 55 is removed from the insert holder 43 and disposed of. A new medicament insert 55 containing a medicament charge is then inserted into the holder 43. Pressure is then exerted against the piston rod 23 to return the piston 19 to its aft position in the cylindrical housing 13 and then the housing 41 is again threaded into the cylindrical housing 13.

As has been illustrated, the patient's tissue is immobilized by using an annular ring of vacuum to draw the patient's tissue tightly over the orifice of a pressure injector prior to discharging it through the dermis or mucosa so as to prevent the trauma of tearing the tissue and the related post-operative pain.

In addition, the replaceable medicament insert 55 with its forward end 61 and orifice 59 provide a completely sanitary and safe means for using the injector on a series of patients or for interchanging the medicaments between injections.

In the alternate embodiments of FIGS. 4–8 forward-end sections 75 may be removed from the nozzle housing 41 after use on one patient and either disposed of and replaced by a new end section 75 or sterilized before treating a second patient. Similarly, the medicament insert 71 may also be disposed of after use on one patient.

The amount of vacuum employed to draw a patient's tissue over the forward end section of the medicament insert 55 is controlled by adjusting the control handle 54 of the vacuum pressure regulator valve 52 with reference to the dial on the regulator 52.

While the invention has been particuarly shown and described with reference to preferred embodiments thereof, it will be understood by those skilled in the art that various alterations in form and detail may be made therein without departing from the spirit and scope of the invention.

The embodiments of the invention in which an exclusive property or privilege is claimed are defined as follows:

1. A needleless vacuum-compression injector comprising:
   a continuous vacuum chamber and a pressurized gas chamber;
   means for drawing a continuous vacuum in said vacuum chamber;
   means for supplying pressurized gas to said pressurized gas chamber;
   means for holding a medicament;
   a nozzle having a passageway connected to said means for holding said medicament and for having said medicament expressed therethrough;
   tissue immobilizing means including an an outwardly extending surface spaced from and surrounding said nozzle wherein said nozzle substantially terminates in the plane of said surface;
   said tissue immobilizing means further including an annular suction means formed in an annular region of said outwardly extending surface and spaced from and surrounding said nozzle, said annular suction means being in continuous communication with said vacuum chamber, said tissue immobilizing means, when positioned against said tissue, being operative to continuously draw said tissue toward said annular region and thereby immobilize and hold said tissue taut over said nozzle without puncturing said tissue and without substantially displacing said tissue from its initial condition;
   means adapted to express said medicament through said passageway and into said tissue upon application of said pressurized gas to said pressurized gas chamber; and,
   wherein said outwardly extending surface is non-circular shaped.

2. The apparatus of claim 1 wherein said outwardly extending surface is oval.

3. A needleless vacuum-compression injector comprising:
   a continuous vacuum chamber and a pressurized gas chamber;
   means for supplying pressurized gas to said pressurized gas chamber;
   means for holding a medicament;
   a nozzle having a passageway connected to said means for holding said medicament and for having said medicament expressed therethrough;
   tissue immobilizing means including an outwardly extending surface spaced from and surrounding said nozzle wherein said nozzle substantially terminates in the plane of said surface;
   said tissue immobilizing means further including an annular suction means formed in an annular region of said outwardly extending surface and spaced from and surrounding said nozzle, said annular suction means being in continuous communication with said vacuum chamber, said tissue immobilizing means, when positioned against said tissue, being operative to continuously draw said tissue toward said said annular region and thereby immobilize and hold said tissue taut over said nozzle without puncturing said tissue and without substantially displacing said tissue from its initial condition;
   means adapted to express said medicament through said passageway and into said tissue upon application of said pressurized gas to said pressurized gas chamber; and,
   wherein said tissue immobilizing means is removable from said injector.

4. A needleless vacuum-compression injector comprising:
   a continuous vacuum chamber and a pressurized gas chamber;
   means for drawing a continuous vacuum in said vacuum chamber;
   means for supplying pressurized gas to said pressurized gas chamber;
   means for holding a medicament;
   a nozzle having a passageway connected to said means for holding said medicament and for having said medicament expressed therethrough;
   tissue immobilizing means including an outwardly extending surface spaced from and surrounding said nozzle wherein said nozzle substantially terminates in the plane of said surface;
   said tissue immobilizing means further including an annular suction means formed in an annular region of said outwardly extending surface and spaced from and surrounding said nozzle, said annular suction means being in continuous communication with said vacuum chamber, said tissue immobilizing means, when positioned against said tissue, being operative to continuously draw said tissue toward said annular region and thereby immobilize and hold said tissue taut over said nozzle without puncturing said tissue and without substantially displacing said tissue from its initial condition;
   means adapted to express said medicament through said passageway and into said tissue upon application of said pressurized gas to said pressurized gas chamber;
   including sleeve means for holding said means for holding said medicament, said sleeve means surrounding said passageway to provide a channel between said sleeve means and said means for holding said medicament for communicating with said vacuum chamber; and,
   spacing means between said means for holding said medicament and said sleeve means for spacing said sleeve from said means for holding said medicament.

5. Apparatus of claim 1 wherein said spacing means is affixed to said medicament holding means.

6. Apparatus of claim 4 wherein said injector includes a housing for holding said means for holding said medicament; and, including, second spacing means for spacing said means for holding said medicament from said housing.

7. Apparatus of claim 6 wherein said second spacing means is affixed to said medicament holding means.

8. Apparatus of claim 6 wherein said sleeve is engageable with said housing, but selectively disengageable therefrom.

9. Apparatus of claim 8 wherein said sleeve is slidably engageable with said housing.

10. Apparatus of claim 8 wherein said sleeve is threadably engageable with said housing.

11. A needleless vacuum-compression injector comprising:
    a continuous vacuum chamber and a pressurized gas chamber;
    means for drawing a continuous vacuum in said vacuum chamber;
    means for supplying pressurized gas to said pressurized gas chamber;
    means for holding a medicament;
    a nozzle having a passageway connected to said means for holding said medicament and for having said medicament expressed therethrough;
    tissue immmobilizing means including an outwardly extending surface spaced from and surrounding said nozzle wherein said nozzle substantially terminates in the plane of said surface;
    said tissue immobilizing means further including an annular section means formed in an annular region of said outwardly extending surface and spaced from and surrounding said nozzle, said annular suction means being in continuous communication with said vacuum chamber, said tissue immobilizing means, when positioned against said tissue, being operative to continuously draw said tissue toward said annular region and thereby immobilize and hold said tissue taut over said nozzle without puncturing said tissue and without substantially displacing said tissue from its initial condition;
    means adapted to express said medicament through said passageway and into said tissue upon application of said pressurized gas to said pressurized gas chamber; and,
    including means for regulating the pressure of said pressurized air to control the depth of penetration of said medicament into said tissue.

12. A needleless method for injecting a medicament through a nozzle and into the tissue of a patient comprising the steps of:
    immobilizing a selected portion of said tissue by continuously applying a vacuum to said tissue in an annular area spaced from the location on said tissue where said medicament is to be injected; and, drawing said selected portion of said tissue over said nozzle and continuously holding said tissue taut without puncturing said tissue and without substantially displacing said tissue from its initial condition;

using a pressurized gas to inject said medicament into said tissue at said location where said tissue is tautly immobilized by the continuous suction applied to said annular area; and, controlling the depth of penetration of said medicament by selectively varying the pressure of said pressurized gas.

* * * * *